US009119763B1

(12) United States Patent
Leary

(10) Patent No.: US 9,119,763 B1

(45) Date of Patent: Sep. 1, 2015

(54) SEX TOY

(71) Applicant: Dan Leary, Shelby, MT (US)

(72) Inventor: Dan Leary, Shelby, MT (US)

(73) Assignee: Dan Leary, Shelby, MT (US)

( * ) Notice: Subject to any disclaimer, the term of this patent is extended or adjusted under 35 U.S.C. 154(b) by 173 days.

(21) Appl. No.: 14/020,834

(22) Filed: Sep. 7, 2013

Related U.S. Application Data

(60) Provisional application No. 61/698,561, filed on Sep. 7, 2012.

(51) Int. Cl.

*A61F 5/00* (2006.01)

*A61H 19/00* (2006.01)

(52) U.S. Cl.

CPC .................................... *A61H 19/00* (2013.01)

(58) Field of Classification Search

CPC ....... A61H 19/00; A61H 19/30; A61H 19/40; A61H 23/0254

USPC ............... 600/38-41; 601/46, 84, 93-95, 101

See application file for complete search history.

(56) References Cited

U.S. PATENT DOCUMENTS

| | | | |
|---|---|---|---|
| 5,853,362 | A | 12/1998 | Jacobs |
| D515,219 | S | 2/2006 | Nan |
| D558,356 | S | 12/2007 | Nan |
| D599,486 | S | 9/2009 | Stewart |
| D603,523 | S | 11/2009 | Nan et al. |
| D626,248 | S | 10/2010 | Gotzen et al. |
| 2003/0093016 | A1 | 5/2003 | Chen |
| 2004/0230093 | A1 | 11/2004 | Marshall |
| 2009/0281373 | A1 | 11/2009 | Mark |
| 2011/0124959 | A1 | 5/2011 | Murison |

*Primary Examiner* — John Lacyk

(74) *Attorney, Agent, or Firm* — IP Law Leaders, PLLC

(57) ABSTRACT

The invention is a sex toy to provide sexual pleasure. More specifically, the invention is directed to a hand-portable sex toy. The sex toy is powered by a pleasure drive assembly located in a housing. The pleasure drive assembly comprises an electric motor, first and second gear assembles, and a cross-shaft with a plurality of discs attached thereto. The electric motor has a through shaft with first and second opposite ends which are respectively operably coupled to first and second gear assemblies. The first and second gear assemblies are operably coupled to the cross-shaft. Upon activation of the motor the discs are rotated to provide sexual pleasure. A flexible cover such as, but not limited to, an elastomeric cover is stretched at least partially over the rotating discs. In normal use the sex toy is inserted into a woman's vagina to provide pleasure.

2 Claims, 14 Drawing Sheets

| TABLE 1 | |
|---|---|
| Part # | Description |
| *B* | at least one battery *B* |
| 100 | sex toy 100 |
| 100L | sex toy 100L, linear version of sex toy 100 |
| 100C | sex toy 100C, has a housing comprising at least one curve |
| 120 | housing 120 |
| 130 | pleasure drive mechanism 130 |
| 135 | battery section 135 |
| 137 | switch 137 |
| 139 | adapter |
| 140 | electric motor 140 |
| 141 | plug 141 |
| 160 | first gear assembly (FGA) 160 |
| 180 | second gear assembly (SGA) 180 |
| 200 | cross-shaft 200 |
| 200C | corrugated version of cross-shaft 200 |
| 202, 204 | first and second opposite cross-shaft ends 202 and 204, respectively |
| 206, 208 | first and second cross-shaft gears 206 and 208 |
| 210 | longitudinal axis 210 of the cross-shaft 200 |
| 220 | plurality of pleasure discs 220 |
| 222 | flexible cover 222 |
| 224 | disc arms 224 |
| 228 | disc groves 228 |
| 240, 260 | first and second opposite motor-ends 240 and 260 of electric motor 140 |
| 280 | output-shaft 280 of electric motor 140 |

*FIG. 13A*

| TABLE 1 (continued) | |
|---|---|
| Part # | Description |
| 300, 320 | opposite first 300 and second 320 output-shaft ends |
| 340, 360 | first FGA end 340, and second FGA end 360 |
| 380 | at least one gear 380 in first gear assembly 160 |
| 400, 420 | first SGA end 400, and second SGA end 420 |
| 440 | at least one gear 440 in second gear assembly 180 |
| 460 | FGA drive gear 460 |
| 480 | FGA idler gear 480 |
| 485 | FGA idler shaft 485 |
| 520 | SGA drive gear 520 |
| 540 | SGA idler gear 540 |
| 545 | SGA idler shaft 545 |

*FIG. 13B*

SEX TOY

CROSS-REFERENCE TO RELATED APPLICATIONS

This application claims the benefit of priority from U.S. Provisional Patent Application Ser. No. 61/698,561, filed Sep. 7, 2012. The entire content of Application Ser. No. 61/698,561 is incorporated herein by reference.

STATEMENT REGARDING FEDERALLY SPONSORED RESEARCH OR DEVELOPMENT

Not Applicable.

FIELD OF THE INVENTION

This invention relates to sexual stimulating devices for providing female sexual pleasure. More specifically, the invention is directed to a stimulator for insertion into a vaginal cavity as a sex aid for providing a woman with sexual pleasure.

BACKGROUND OF THE INVENTION

As the muscles of the vaginal wall lose their tautness and as the vagina enlarges so that vaginal tightness decreases, the female may experience a decrease in sexual satisfaction and sensation. Also, women often desire sexual pleasure but don't want to engage in risky or casual sex. There is a continuing need for devices that address such issues.

United States Patent Application Publication Number 20030093016 describes a massager with a rotation shaft having arcuate grooves defined in a periphery of the rotation shaft and a guide received in the arcuate grooves so that when the rotation shaft rotates, the guide is able to control the rotation shaft to rotate and extend.

United States Patent Application Publication Number 20090281373 describes a sexual aid device and method for inserting and occupying space within a human female's vagina to provide a sensation of increased fullness to the female and a sensation of increased tightness and friction to a penis of a human male during sexual intercourse, thereby enhancing sexual arousal of both the female and the male. The sexual aid can be a member having a bulbous end for insertion and a tapered end for externally grasping and manipulating the member. The tapered end may include a hooked protrusion for providing anal stimulation to the female. The member may contain one or more vibrating devices. The member may further include a generally planar surface featuring a trough and can include two arced terminuses oriented in opposing directions. An internal pellet-rotating device may be installed within the tapered end of the member to produce mechanical friction in and around the vagina.

U.S. Design Pat. No. D515219 discloses the ornamental design for an attachment sleeve for a vibrator head. The sleeve comprises a plurality of protrusions to provide additional sexual stimulation to a female in need of such stimulation.

None of the above inventions and patents, taken either singly or in combination, is seen to describe the instant invention as claimed.

SUMMARY OF THE INVENTION

The invention is a sex toy to provide sexual pleasure. More specifically, the invention is directed to a hand-portable sex toy. The sex toy is powered by a pleasure drive assembly located in a housing. The pleasure drive assembly comprises an electric motor, first and second gear assembles, and a cross-shaft with a plurality of discs attached thereto. The electric motor has a through shaft with first and second opposite ends which are respectively operably coupled to first and second gear assemblies. The first and second gear assemblies are operably coupled to the cross-shaft. Upon activation of the motor the discs are rotated to provide sexual pleasure. An elastomeric cover is stretched over the rotating discs. In normal use the sex toy is inserted into a woman's vagina to provide pleasure.

BRIEF DESCRIPTION OF THE DRAWINGS

FIGS. 13A and 13B show a table (Table 1) that lists reference numbers and their associated descriptions.

Similar reference characters denote corresponding features consistently throughout the attached drawings.

DETAILED DESCRIPTION OF THE PREFERRED EMBODIMENTS

Figure 1:
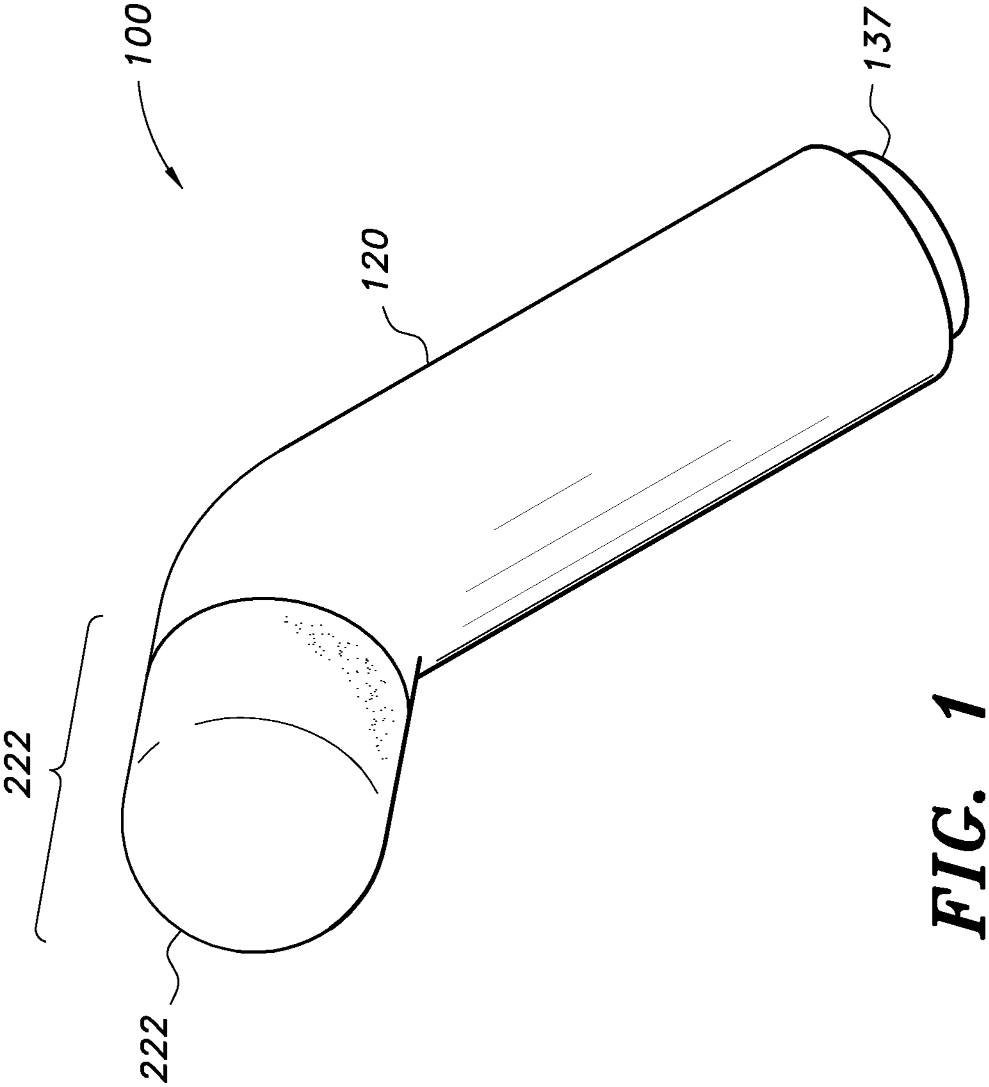
FIG. 1 shows an external view of a sex toy according to at least one embodiment of the present invention.

This invention relates to sexual stimulating devices for providing female sexual pleasure. More specifically, the invention is a sex toy 100 for insertion into a vaginal cavity as a sex aid for providing a woman with sexual pleasure. A summary of the component parts are listed in Table 1 (see FIGS. 13A and 13B).

With reference to FIGS. 1 through 12, the sex toy 100 includes a housing 120, a pleasure drive mechanism 130, and a battery section 135 for accommodating at least one battery B. The pleasure drive mechanism 130 comprises an electric motor 140, a first gear assembly 160, a second gear assembly 180, a cross-shaft 200, and a plurality of pleasure discs 220. A flexible cover 222 such as, but not limited to an elastomeric cover, at least partially covers the pleasure discs 220. The housing 120 can have any suitable exterior shape. For example, in FIG. 2 the housing 120 includes a curve (in this Figure the sex toy is represented overall by label "100*c*"); in FIG. 3 the housing 120 is elongated and essentially appears straight to the naked eye.

A suitable switch 137 is used to switch the sex toy 100 on and off. The sex toy 100 can be powered by an external source such as a wall AC outlet using, for example, an adapter 139 (for stepping down the AC voltage and converting it to DC) and a suitable plug 141; see FIGS. 8 through 12. Hence, the battery section 135 is optional and may be dispensed with if the sex toy 130 is provided in combination with an adapter 139 and plug connection 141.

Figure 2:
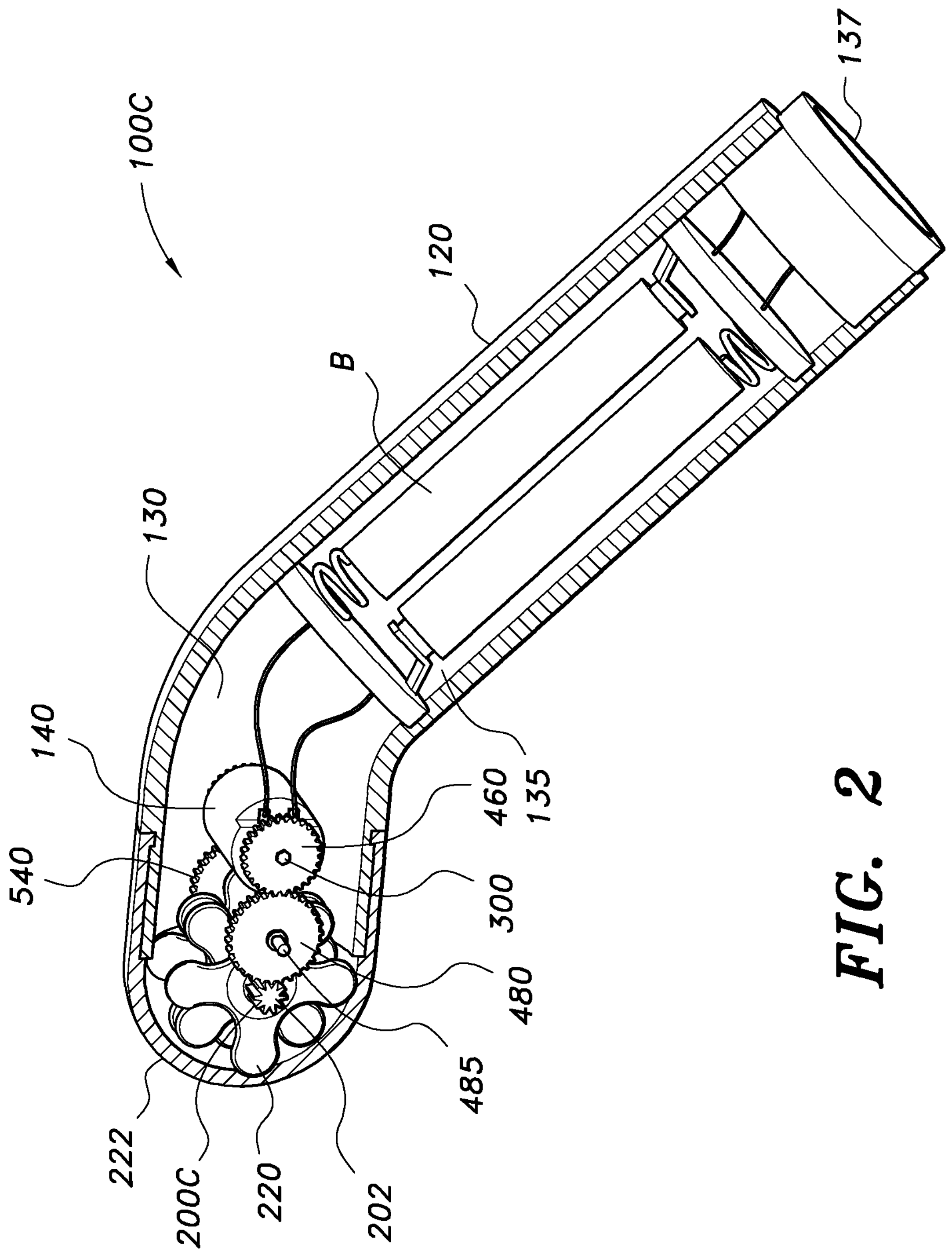
FIG. 2 shows an internal view of a sex toy according to one embodiment of the present invention.
Figure 3:
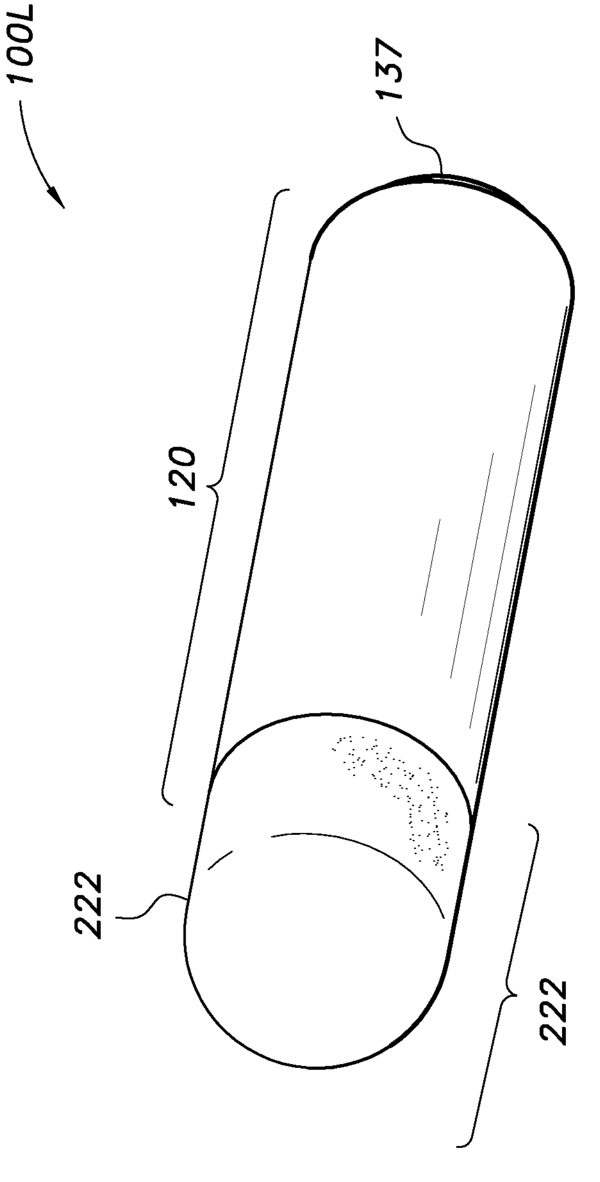
FIG. 3 shows an external view of a sex toy according to at least one embodiment of the present invention.
Figure 4:
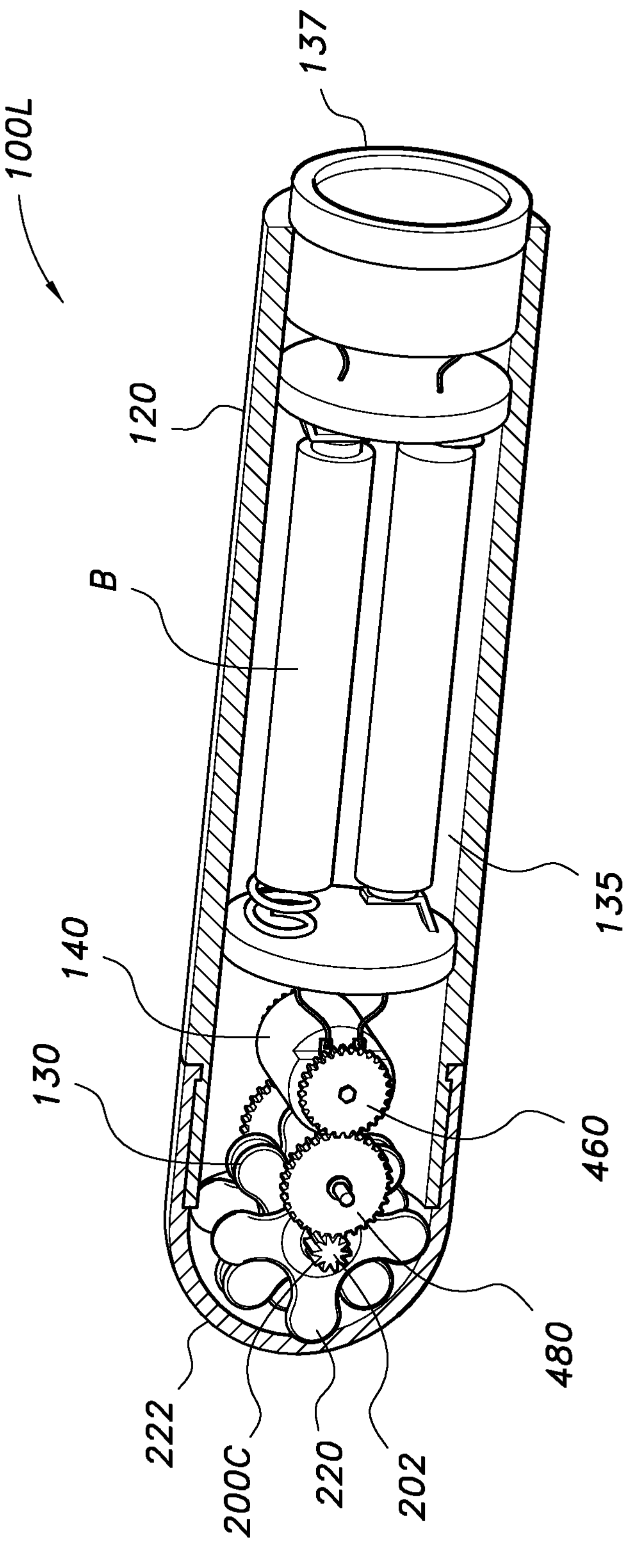
FIG. 4 shows an internal view of a sex toy according to one embodiment of the present invention.
Figure 4A:
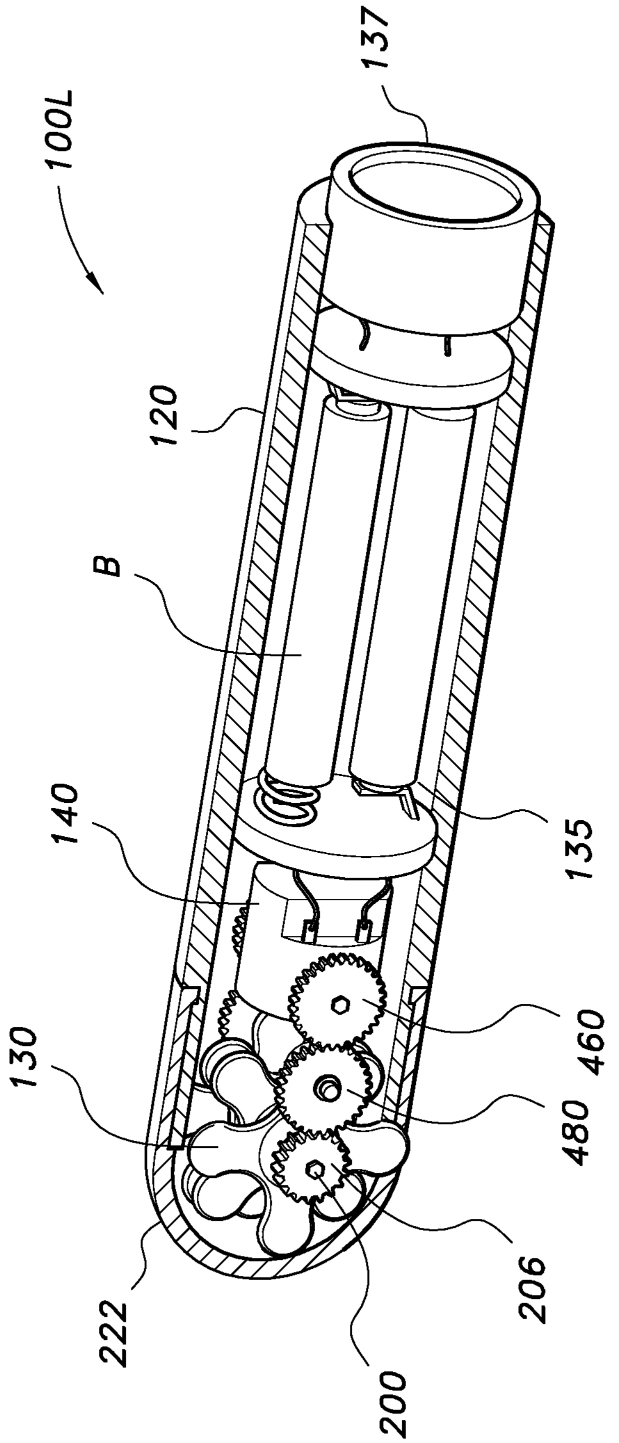
FIG. 4A shows an internal view of a sex toy according to one embodiment of the present invention.

The terms "first gear assembly" and "second gear assembly" are respectively abbreviated to "FGA" and "SGA", respectively. As noted previously, the housing 120 can have any suitable shape such as, but not limited to, an elongated shape as shown in FIG. 3, or an elongated shape incorporating a curved shape as shown in FIG. 2.

The cross-shaft 200 defines first and second opposite cross-shaft ends 202 and 204, respectively; the cross-shaft 200 has a longitudinal axis 210. The cross-shaft 200 having a plurality of the pleasure discs 220 (of constant or varying diameters) attached to the cross-shaft 200, the discs 220 are shown (for example, in FIG. 5A) having a perpendicular angle with respect to the longitudinal axis 210 of the cross-shaft 200. However, the discs 220 may be attached to the cross-shaft at varying angles (i.e., at non-perpendicular angles) with respect to the longitudinal axis 210 of the cross-shaft 200. Also, a mixture of discs 220 with perpendicular and non-perpendicular angles with respect to the axis 210. The discs 220 can be made up of constant diameters or varying diameters. The discs 220 can be circular or non-circular. For example, in FIG. 5 the discs comprise arms 224 with concave disc grooves 228 located between the arms 224. A combination of discs with varying diameters and disc shapes aid in providing sexual pleasure. The cross-shaft 200, first and second gear assemblies 160 and 180, and the motor 140 define a generally rectangular configuration.

Figure 5:
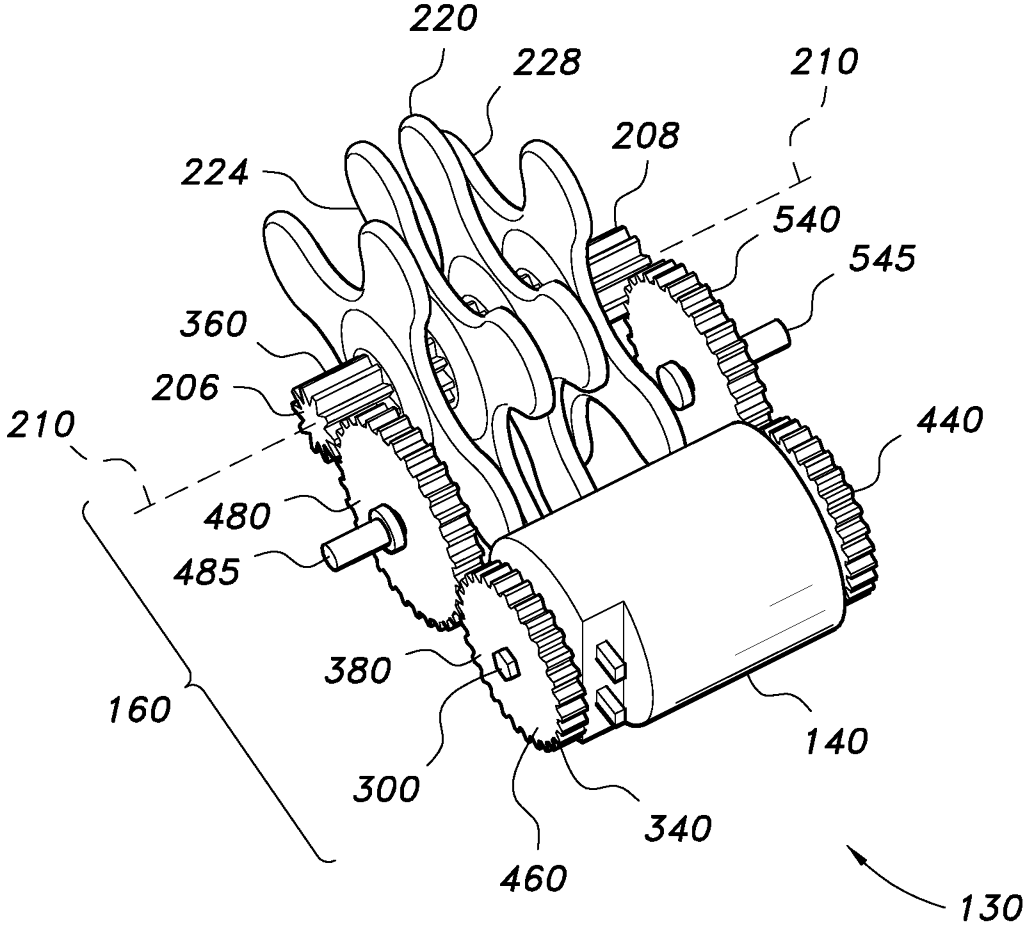
FIG. 5 shows a view of a pleasure drive mechanism according to one embodiment of the present invention.

It should be noted however that the parts shown in the drawings are not limited to the exact size or shape. For example, the motor 140 can be any suitable shape such as that shown in FIGS. 5 and 5C. In FIG. 5 the motor 140 is generally cylindrical in shape whereas in FIG. 5C the motor 140 is of a different shape.

The first and second opposite ends 202 and 204 of the cross-shaft 200 can be corrugated (labelled as "200C" in, e.g., FIG. 2) to enable the ends 202 and 204 to mesh with and be rotated respectively by gears 480 and 540. With respect to FIGS. 5A and 5B the first gear assembly (FGA) 160 is made up of FGA drive gear 460, and FGA idler gear 480; and the second gear assembly (SGA) 180 is made up of SGA drive gear 520, and SGA idler gear 540. The cross-shaft 200 may be corrugated along its entire length or just at the ends 202 and 204.

Figure 5A:
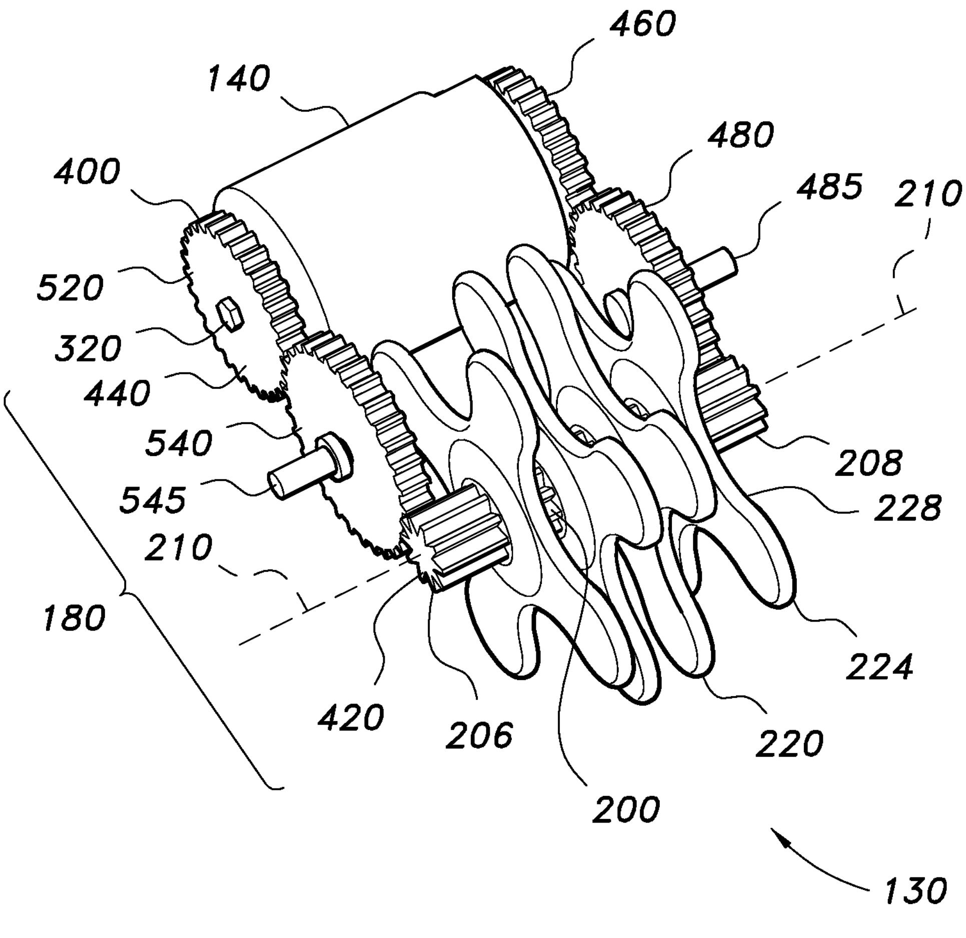
FIG. 5A shows a view of the pleasure drive mechanism of FIG. 5.
Figure 5B:
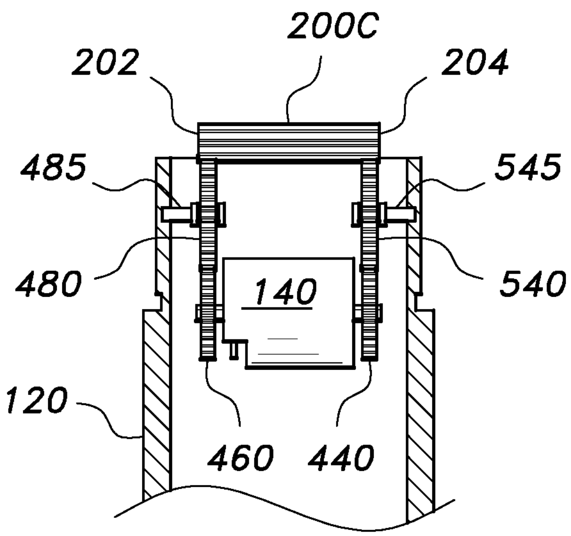
FIG. 5B shows a partial cut-away elevated view of the pleasure drive mechanism of FIG. 5 in which pleasure discs 220 are not show in order to give a view of a corrugated version of the cross-shaft 200.
Figure 5C:
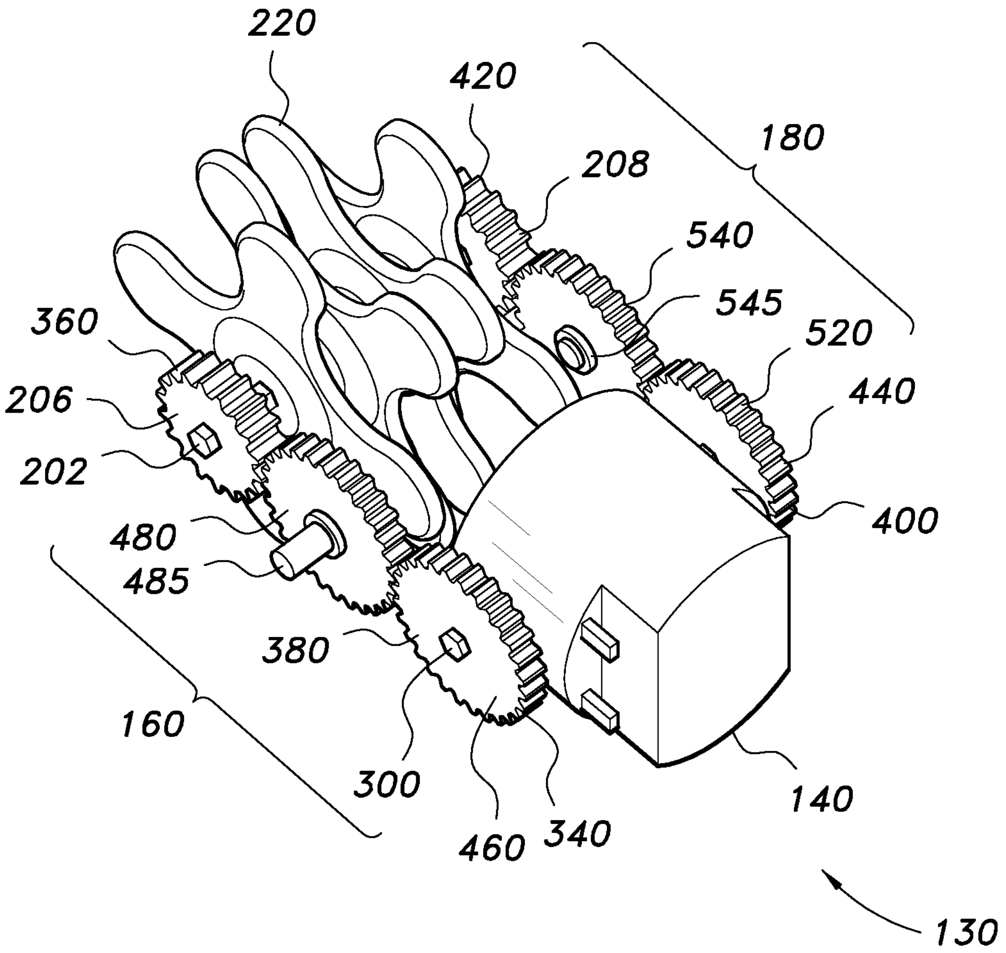
FIG. 5C shows a view of a pleasure drive mechanism according to one embodiment of the present invention.
Figure 6:
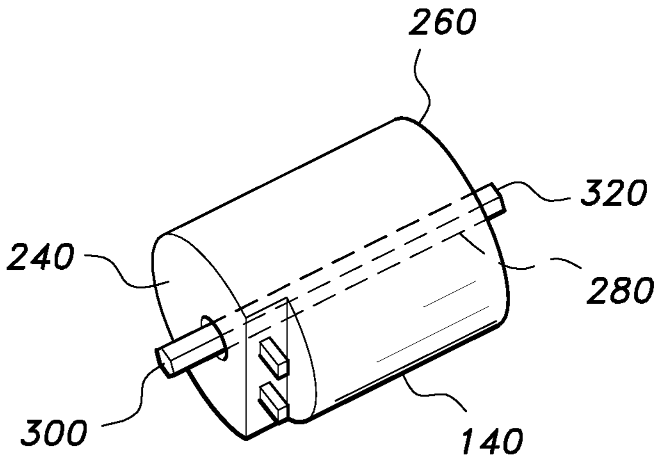
FIG. 6 shows an external view of an electric motor with an output-shaft that extends through the motor.
Figure 7:
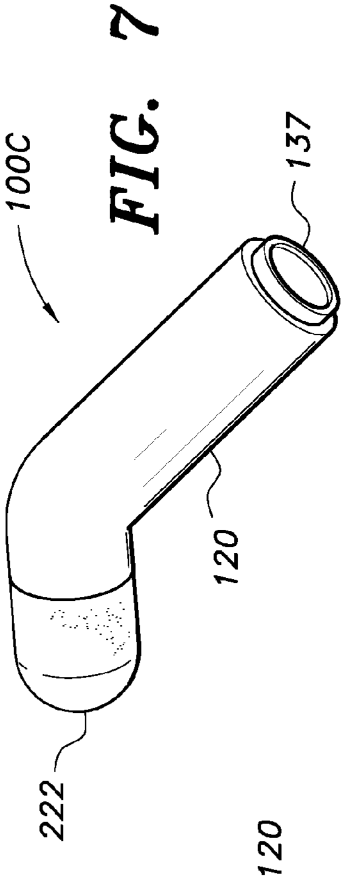
FIG. 7 shows an external view of a sex toy according to at least one embodiment of the present invention.
Figure 8:
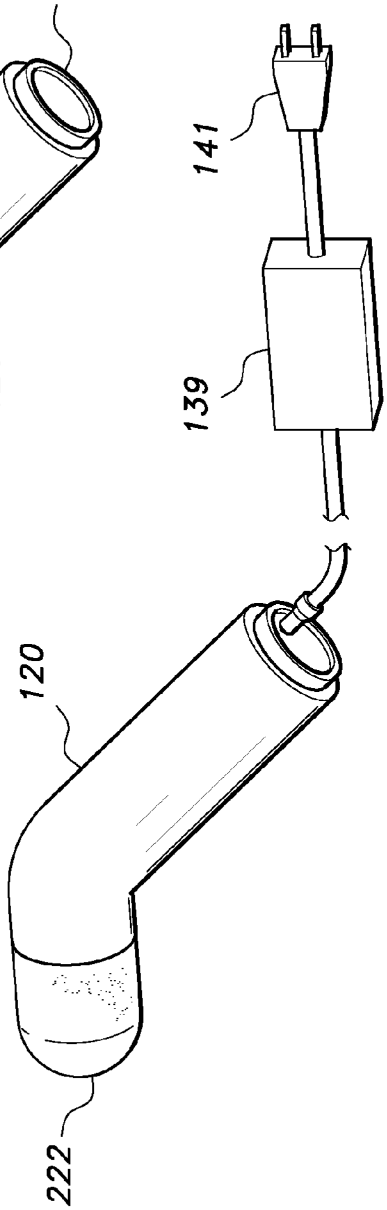
FIGS. 8 and 9 show further external views of a sex toy according to at least one embodiment of the invention.
Figure 9:
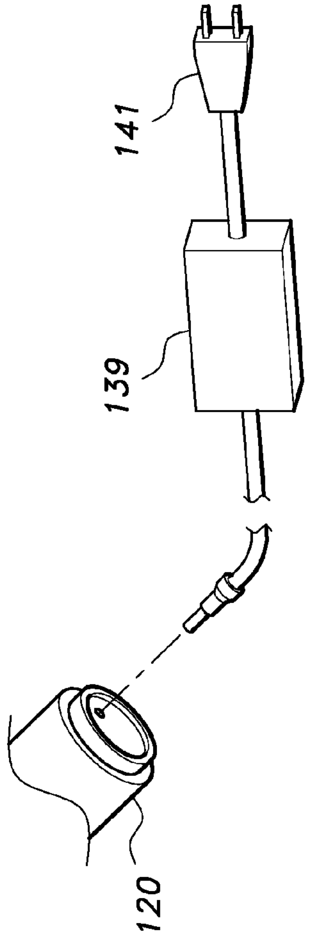
Figure 10:
FIG. 10 shows an external view of a sex toy according to at least one embodiment of the present invention.
Figure 11:
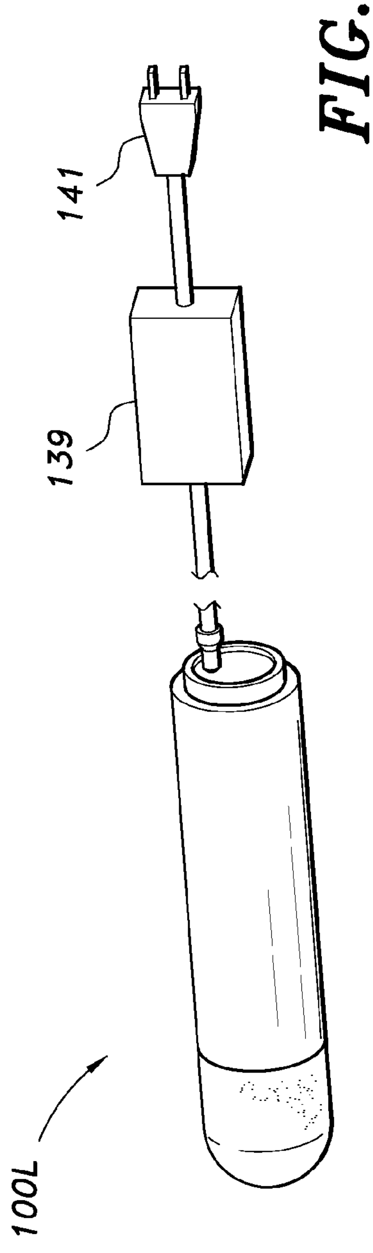
FIGS. 11 and 12 show further external views of a sex toy according to at least one embodiment of the invention.
Figure 12:
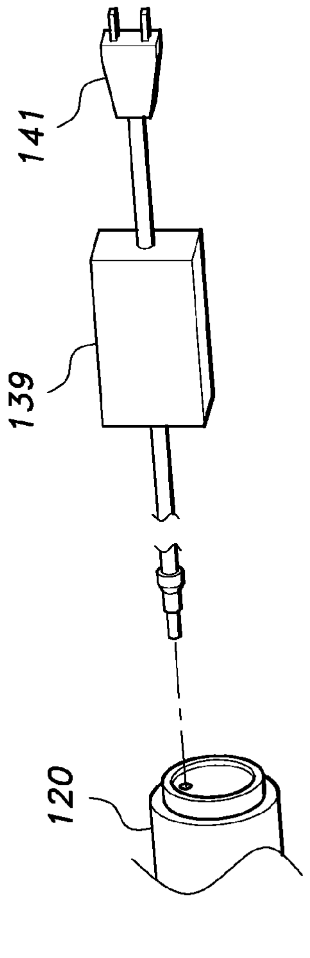

In the alternative, the ends 202 and 204 can be fitted with first and second cross-shaft gears 206 and 208 respectively; the first and second cross-shaft gears 206 and 208 mesh with and are driven by gears 480 and 540, respectively (see FIGS. 5 and 5A). With respect to FIG. 5C the first gear assembly (FGA) 160 is made up of first cross-shaft gear 206, FGA drive gear 460, and FGA idler gear 480; and the second gear assembly (SGA) 180 is made up of second cross-shaft gear 208, SGA drive gear 520, and SGA idler gear 540.

The electric motor 140 has first and second opposite motor-sides 240 and 260, respectively. The electric motor 140 has an output-shaft 280 that extends through the electric motor 140 such that the output-shaft 280 protrudes from both the first and second opposite motor-sides 240 and 260 of the electric motor 140. The output-shaft 280 has opposite first 300 and second 320 output-shaft ends. The opposite first 300 and second 320 output-shaft ends respectively protrude from the first and second opposite motor-sides 240 and 260 of electric motor 140.

The first gear assembly (FGA) 160 defines first FGA end 340, and second FGA end 360. The first FGA 340 is operatively coupled to the first output-shaft end 300 protruding from the first motor-side 240 of the electric motor 140. The second FGA end 360 is operatively coupled to the first end 202 of the cross-shaft 200. The first gear assembly 160 comprises at least one gear 380. The first gear assembly 160 is perpendicular to the output-shaft 280 and the cross-shaft 200.

The second gear assembly (SGA) 180 defines first SGA end 400, and second SGA end 420. The first SGA end 400 is operatively coupled to the second output-shaft end 320 of output-shaft 280 protruding from the second motor-side 260 of the electric motor 140. The second SGA end 420 is operatively coupled to the second end 204 of the cross-shaft 200. The second gear assembly 180 comprises at least one gear 440. The second gear assembly 180 is perpendicular to the output-shaft 280 and the cross-shaft 200. The second gear assembly 180 is generally parallel to the first gear assembly 160.

The cross-shaft 200, first and second gear assemblies 160 and 180, and the motor 140 define a generally rectangular configuration in which the first and second gear assemblies 160 and 180 are parallel to each other, and the cross-shaft 200 is parallel to the output-shaft 280 of the motor 140.

For convenience the abbreviation "SGA" is regarded as equivalent to the term "second gear assembly"; and the abbreviation "CS" is regarded as equivalent to the term "cross-shaft".

The first gear assembly 160 includes an FGA drive gear 460. The FGA drive gear 460 is securely attached to, or otherwise integral with, the first output-shaft end 300 of output-shaft 280. In turn the FGA drive gear 460 is operably coupled to an FGA idler gear 480. The FGA idler gear 480 is coupled to a first CS gear 206 located at the first end 202 of cross-shaft 200. The first CS gear 206 is securely attached to, or forms an integral with, cross-shaft 200. The FGA idler gear 480 rotates freely on FGA idler shaft 485; the idler shaft 485 can be molded into the inside of the housing 120. The principles by which an idler gear rotates on a shaft is explained in U.S. Pat. No. 6,902,525 (issued to Jewel on Jun. 7, 2005); see, column 6, lines 38-40 therein. U.S. Pat. No. 6,902,525 is herein incorporated by reference in its entirety.

The second gear assembly 180 includes an SGA drive gear 520. The SGA drive gear 520 is securely attached to, or otherwise integral with, the second output-shaft end 320 of output-shaft 280. In turn the SGA drive gear 520 is operably coupled to an SGA idler gear 540. The SGA idler gear 540 is coupled to a second CS gear 208 located at the second end 204 of cross-shaft 200. The second CS gear 208 is securely attached to, or is an integral part of, cross-shaft 200. The SGA idler gear 540 rotates freely on SGA idler shaft 545; the idler shaft 545 can be molded into the inside of the housing 120.

The invention being thus described, it will be evident that the same may be varied in many ways by a routineer in the applicable arts. Such variations are not to be regarded as a departure from the spirit and scope of the invention.

What is claimed:

1. A pleasure drive mechanism for use in a sex toy, comprising:

an electric motor, the electric motor having first and second opposite motor-sides, the electric motor having an output-shaft, the output-shaft having opposite first and second output-shaft ends, the output-shaft extending completely through the electric motor such that opposite first and second output-shaft ends respectively protrude from the first and second opposite motor-sides of the electric motor;

a cross-shaft, the cross-shaft having first and second opposite cross-shaft ends, the cross-shaft defining a longitudinal axis, the cross-shaft having a plurality of pleasure discs attached to the cross-shaft, the cross-shaft being parallel to the output-shaft of the motor;

a first gear assembly (FGA), the first gear assembly has first and second FGA ends, the first FGA end is operatively coupled to the first output-shaft end, the second FGA end is operatively coupled to the first cross-shaft end, the first gear assembly is perpendicular to the output-shaft and the cross-shaft, and a second gear assembly (SGA), the second gear assembly has first and second SGA ends, the first SGA end is operatively coupled to the second output-shaft end, the second SGA end is operatively coupled to the second cross-shaft end, the second gear assembly is parallel to the first gear assembly, the second gear assembly is perpendicular to the output-shaft and the cross-shaft.

2. A sex toy, comprising:

a pleasure drive mechanism, wherein the pleasure drive mechanism comprises:

an electric motor, the electric motor having first and second opposite motor-sides, the electric motor having an output-shaft, the output-shaft having opposite first and second output-shaft ends, the output-shaft extending completely through the electric motor such that opposite first and second output-shaft ends respectively protrude from the first and second opposite motor-sides of the electric motor, a cross-shaft, the cross-shaft having first and second opposite cross-shaft ends, the cross-shaft defining a longitudinal axis, the cross-shaft having a plurality of pleasure discs attached to the cross-shaft, the cross-shaft being parallel to the output-shaft of the motor, a first gear assembly (FGA), the first gear assembly has first and second FGA ends, the first FGA end is operatively coupled to the first output-shaft end, the second FGA end is operatively coupled to the first cross-shaft end, the first gear assembly is perpendicular to the output-shaft and the cross-shaft, and a second gear assembly (SGA), the second gear assembly has first and second SGA ends, the first SGA end is operatively coupled to the second output-shaft end, the second SGA end is operatively coupled to the second cross-shaft end, the second gear assembly is parallel to the first gear assembly, the second gear assembly is perpendicular to the output-shaft and the cross-shaft;

a flexible cover; and a housing, wherein the pleasure drive mechanism is located in the housing except that the flexible cover extends over the plurality of pleasure discs.

* * * * *